United States Patent [19]

Howe et al.

[11] 4,401,457

[45] Aug. 30, 1983

[54] 3'-(SUBSTITUTED PHENYL)-SPIRO[ISOBENZOFURAN-1(3H),5'(4'H)-ISOXAZOL]-3-ONES AND THEIR USE AS HERBICIDES

[75] Inventors: Robert K. Howe, Bridgeton; Kou-Chang Liu, Creve Coeur, both of Mo.

[73] Assignee: Monsanto Company, St. Louis, Mo.

[21] Appl. No.: 422,773

[22] Filed: Sep. 24, 1982

Related U.S. Application Data

[62] Division of Ser. No. 160,692, Jun. 18, 1980, Pat. No. 4,364,768, which is a division of Ser. No. 971,462, Dec. 20, 1978, Pat. No. 4,209,629.

[51] Int. Cl.³ ............................................. A01N 43/50
[52] U.S. Cl. ............................................. 71/88; 71/76
[58] Field of Search ............................................. 71/88

[56] References Cited

U.S. PATENT DOCUMENTS

| | | | |
|---|---|---|---|
| 3,947,263 | 3/1976 | Brouwer et al. | 71/88 |
| 3,964,896 | 6/1976 | Brouwer et al. | 71/92 |
| 4,032,644 | 6/1977 | Nadelson | 548/247 |

FOREIGN PATENT DOCUMENTS 1494877  12/1977  United Kingdom .

*Primary Examiner*—Catherine L. Mills
*Attorney, Agent, or Firm*—Richard H. Shear; J. Timothy Keane

[57] ABSTRACT

3'-(Substituted phenyl)-spiro[isobenzofuran-1(3H),5'(4'H)-isoxazol]-3-ones have been found to be effective as herbicides and plant growth regulants, especially for the regulation of soybean

11 Claims, No Drawings

3'-(SUBSTITUTED PHENYL)-SPIRO[ISOBENZOFURAN-1(3H),5'(4'H)-ISOXAZOL]-3-ONES AND THEIR USE AS HERBICIDES

This is a division of application Ser. No. 160,692, filed June 18, 1980, now U.S. Pat. No. 4,364,768, which is a division of Ser. No. 971,462, filed Dec. 20, 1978 and now U.S. Pat. No. 4,209,629.

This invention relates to compounds useful as herbicides and plant growth regulants. The compounds may be represented by the formula

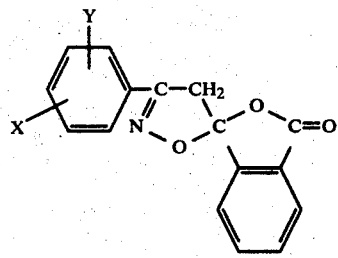

(I)

wherein X and Y are independently selected from the group consisting of hydrogen, halogen, lower alkyl, lower alkoxy, halo-lower-alkyl, phenoxy, phenyl and cyano.

The terms "lower alkyl" and "lower alkoxy" as used herein are understood to include those alkyl and alkoxy groups having up to five carbon atoms, inclusive. Both straight as well as branched chain alkyl groups are contemplated.

The term "halo-lower-alkyl" as used herein is understood to mean those lower alkyl groups in which at least one, and perhaps all, of the hydrogen atoms have been replaced by halogen atoms. It is to be clearly understood that trifluoromethyl is contemplated as being a halo-lower alkyl moiety.

The term "halogen" as used herein includes chlorine, bromine, fluorine and iodine.

In accordance with one of the novel aspects of the present invention, the compounds of the foregoing formula may be prepared by the reaction of the appropriate nitrile oxide with 3-methylenephthalide.

The reaction readily proceeds at room temperature and atmospheric pressure although slightly elevated temperatures and pressures may be utilized to increase the rate of reaction. Although the nitrile oxide may be generated separately and then reacted with 3-methylenephthalide, it has been found to be convenient to generate the nitrile oxide in situ by reacting an appropriate chlorooxime with 3-methylenephthalide under basic conditions as follows:

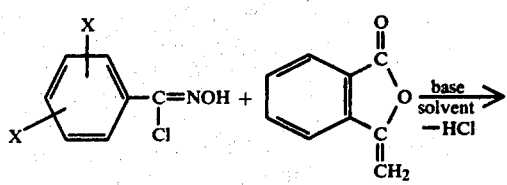

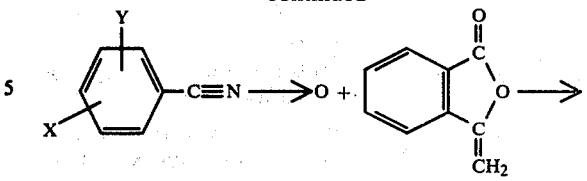

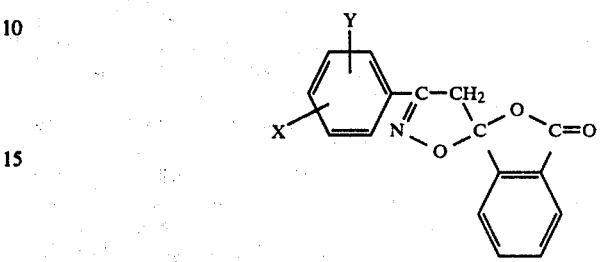

This reaction proceeds at room temperature and atmospheric pressure although slightly elevated temperatures and pressures may be utilized. Normally, an equimolar ratio of reactants is utilized. When the nitrile oxide is relatively unstable, a large excess of chlorooxime may be utilized. Under most conditions, a slight excess is preferred. The molar ratio to be utilized with any given reaction is within the skill of the art. As noted, the reaction proceeds under basic conditions. Bases such as tertiary amines are preferred. Especially preferred is the use of a stoichiometric amounts of triethylamine. Any inert solvent in which the reactants are readily soluble may be utilized. These include ether, dimethylformamide, tetrahydrofuran, chloroform, carbon tetrachloride, methylene chloride, dioxane and the like.

Chlorooximes are known in the art and are readily prepared by reaction of hydroxylamine with the appropriate aryl aldehyde in aqueous alcohol, followed by chlorination of the resultant oxime in accordance with the following scheme:

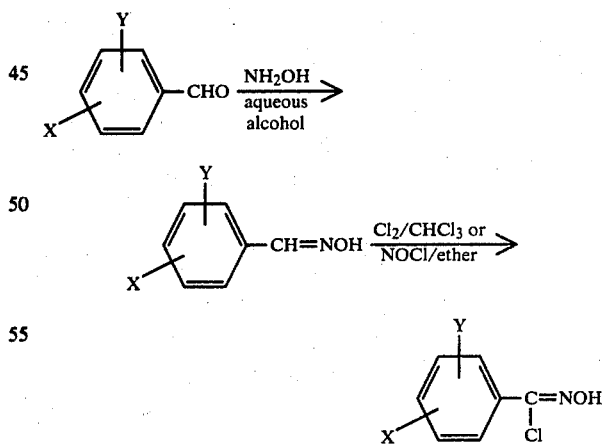

Aryl aldehydes may be prepared by the procedure of Jolad and Rajagopal, *Org. Syn. Coll.,* Vol. V, Page 139 (1973). The procedure of S. V. Vinogradova et al., J. Appl. Chem. (USSR), 44, 1405 (1971) may be used to prepare 3-methylenephthalide. In order to illustrate the above procedure, the following examples are presented. These examples are merely illustrative and are not intended as a limitation on the scope of the invention.

EXAMPLE 1

Preparation of 3'-(3-Biphenylyl)-Spiro[Isobenzofuran-1(3H),5'(4'H)-Isoxazol]-3-One To a solution of 4-biphenylylcarboxaldehyde chlorooxime (34.8 g, 0.15 mole) and 3-methylenephthalide (14.6 g, 0.1 mole) in 450 ml. of ether was added dropwise triethylamine (15.18 g, 0.15 mole) at 5° C. in 20 minutes. The resultant mixture was stirred at room temperature for 20 hours. The solid was then filtered off. The ethereal solution contained a very small amount of the desired spiro compound according to an NMR analysis. The solid material which was filtered off from the original ether solution was extracted twice with 1200 ml. of chloroform. The chloroform solution was washed twice with water, dried over $CaSO_4$ and concentrated under vacuum to give 24.7 g (72.4%) of a beige solid; m.p. 152°–159° C. with decomposition. Recrystallization of 3.5 g of the beige solid from 100 ml. of chloroform gave 1.47 g of white solid; m.p. 170°–172° C. with decomposition.

Anal. Calc'd. for $C_{22}H_{15}NO_3$: C, 77.41; H, 4.43. Found: C, 77.36; H, 4.45.

EXAMPLE 2

Preparation of 3'-(4-Chlorophenyl)-Spiro[Isobenzofuran-1(3H),5'(4'H)-Isoxazol]-3-One To a solution of 17 g (0.089 mole) of p-chlorobenzaldehyde chlorooxime and 14.0 g (0.096 mole) 3-methylenephthalide in 300 ml. of ether was added 9.0 g (0.089 mole) of triethylamine in 50 ml. of ether at 0°–5° C. during 1 hour. The solution was then allowed to react at room temperature for 20 hours. An infrared spectrum of an aliquot indicated that the reaction was complete. The solid was filtered off. The ethereal solution was washed three times with sodium chloride saturated water, dried over $CaSO_4$ and concentrated under vacuum. Only 2 g of impure product was obtained. The solid material which was filtered off from the original solution was added to 500 ml. of chloroform and washed three times with water. The chloroform solution was cloudy even after 200 ml. of tetrahydrofuran had been added. The chloroform-tetrahydrofuran solution was then dried over $CaSO_4$, filtered and concentrated under vacuum to afford 10.2 g of pale yellow solid (38.2%); m.p. 158°–160° C. A colorless solid, m.p. 166°–167° C., was obtained after several washes with ether.

Anal. Calc'd. for $C_{16}H_{10}NClO_3$ 0 C, 64.12; H, 3.36; N, 4.67; Cl, 11.83. Found: C, 64.14; H, 3.37; N, 4.67; Cl, 11.81.

EXAMPLE 3

Preparation of 3'(2-Methylphenyl)-Spiro[Isobenzofuran-1(3H),5'(4'H)-Isoxazol]-3-One To a solution of o-tolualdehyde chlorooxime (26.8 g, 0.158 mole), 3-methylenephthalide (14.6 g, 0.1 mole) and ether (400 ml.) was added dropwise a solution of triethylamine (16 g, 0.158 mole) in 30 ml. of ether at 5°–10° C. in 45 minutes. The mixture was stirred at room temperature for 40 hours and filtered. The solid material collected was dissolved in 1 liter of chloroform and 200 ml. of water. The chloroform solution was then washed two times with water, dried over $CaSO_4$ and concentrated under vacuum to give 16.4 g of white solid, m.p. 146°–149° C. The original ether solution was washed two times with water, dried over $CaSO_4$ and concentrated to 100 ml. Another 1.64 g of the spiro compound precipitated out. The ether solution was then further concentrated to 10.8 g of yellow-brown oil which did not contain a significant amount of the desired product. Recrystallization of 12 g of the crude spiro compound from tetrahydrofuran-ether gave 9.87 g of a pure white solid, m.p. 159°–164° C. with decomposition.

Anal. Calc'd. for $C_{17}H_{13}NO_3$: C, 73.11; H, 4.69. Found: C, 73.06; H, 4.74.

EXAMPLE 4

Preparation of 3'-(3-Cyanophenyl)-Spiro[Isobenzofuran-1(3H),5'(4'H)-Isoxazol]-3-One 3'-(3-Cyanophenyl)-spiro[isobenzofuran-1(3H)-isoxazol]-3-one was prepared according to the procedure of Example 3 in 62.7% isolated yield. The spiro compound obtained was a white solid, m.p. 134°–137° C. Recrystallization of 12 g of crude spiro compound from tetrahydrofuran-toluene afforded 6.48 g of white solid, m.p. 165°–167° C.

Anal. Calc'd. for $C_{17}H_{10}N_2O_3$: C, 70.34; H, 3.67. Found: C, 70.07; H, 3.50.

EXAMPLE 5

Preparation of 3'-(4-Trifluoromethylphenyl)-Spiro[Isobenzofuran-1(3H),5'(4'H)-Isoxazol]-3-One 3'-(4-trifluoromethylphenyl)-spiro[isobenzofuran-1(3H),5'(4'H)-isoxazol]-3-one was prepared according to the procedure of Example 3 in 36.8% isolated yield. Recrystallization of 5 g of the crude spiro product from 75 ml. of tetrahydrofuran and 50 ml. of ether gave 3.83 g of pure product as white crystals, m.p. 177°–178° C.

Anal. Calc'd. for $C_{17}H_{10}F_3NO_3$: C, 61.27; H, 3.02. Found: C, 61.29; H, 3.06.

EXAMPLE 6

Preparation of 3'-(2-Trifluoromethylphenyl)-Spiro[Isobenzofuran-1(3H),5'(4'H)-Isoxazol]-3-One 3'-(2-trifluoromethylphenyl)-spiro[isobenzofuran-1(3H),5'(4'H)-isoxazol]-3-one was prepared in 35.2% isolated yield according to the procedure of Example 3. The crude spiro product obtained was a white solid, m.p. 149°–150.5° C. Recrystallization of 5 g of the solid from tetrahydrofuran (50 ml.) and ether (50 ml.) afforded 4.12 g of colorless needles, m.p. 156°–157.5° C.

Anal. Calc'd. for $C_{17}H_{10}F_3NO_3$: C, 61.27; H, 3.02. Found: C, 61.24; H, 3.05.

EXAMPLE 7

Preparation of 3'-(3-Methoxyphenyl)-Spiro[Isobenzofuran-1(3H),5'(4'H)-Isoxazol]-3-One 3'-(3-methoxyphenyl)-spiro[isobenzofuran-1(3H),5'(4'H)-isoxazol]-3-one was prepared following the procedure of Example 3. The original ether solution was washed two times with water, dried over $CaSO_4$ and concentrated to 29.6 g of thick oil. The oil contained 50% of the spiro product according to NMR analysis. Isolation of the spiro compound from the oil was not attempted. The solid material which was filtered off from the original ether solution afforded after workup, 5.56 g (18.8% yield) of the desired product as a yellow solid, m.p. 119.5°–123° C. Recrystallization of the solid from tetrahydrofuran-ether gave 4.3 g of a pale yellow solid, m.p. 124°–126° C. with decomposition.

Anal. Calc'd. for $C_{17}H_{13}NO_4$: C, 69.15; H, 4.44. Found: C, 69.03; H, 4.50.

EXAMPLE 8

Preparation of 3'-(3-Phenoxyphenyl)-Spiro[Isobenzofuran-1(3H),5'(4'H)-Isoxazol]-3-One 3'-(3-phenoxyphenyl)-spiro[isobenzofuran-1(3H), 5'(4'H)-isoxazol]-3-one was prepared in 53.9% isolated yield according to the procedure of Example 3. The crude spiro compound isolated was a yellow oil. Purification of 7.9 g of the oil by high pressure liquid chromatography on silica gel with 50% ethyl acetate—50% hexane as the eluant gave 4.2 g of the desired product as a white solid, m.p. 114°–116° C.

EXAMPLE 9

Preparation of 3'-(3-Chlorophenyl)-Spiro[Isobenzofuran-1(3H),5'(4'H)-Isoxazol]-3-One 3'-(3-chlorophenyl)-spiro[isobenzofuran-1(3H),5'(4'H)-isoxazol]-3-one was prepared in 86.4% isolated yield according to the procedure of Example 3. The crude product was a gummy material. Recrystallization of 19 g of the gummy material from tetrahydrofuran-ether gave 5.2 g of solid, m.p. 119°–125° C. A sample of 3.5 g of the solid was purified further by high pressure liquid chromatography on a silica gel column with 50% hexane—50% ethyl acetate as eluant to give 1.77 g of the desired product as a white solid, m.p. 127°–129° C.

Anal. Calc'd. for $C_{16}H_{10}ClNO_3$: C, 64.12; H, 3.36. Found: C, 63.88; H, 3.40.

EXAMPLE 10

Preparation of 3'(2,4-Dichlorophenyl)-Spiro[Isobenzofuran-1(3H),5'(4'H)-Isoxazol]-3-One By a method similar to the procedure of Example 2, a reaction of 2,4-dichlorobenzaldehyde chlorooxime and 3-methylenephthalide was carried out. The solid collected from the reaction mixture afforded 12.2 g of the desired product after workup, and the ether solution gave 4 g of the desired product (yield 70.2%). Recrystallization from chloroform led to pure white crystals of the desired product, m.p. 158°–161° C.

Anal. Calc'd. for $C_{18}H_{13}NCl_2O_3$: C, 57.86; H, 2.73. Found: C, 57.63; H, 2.74.

EXAMPLE 11

Preparation of 3'-Phenyl-Spiro[Isobenzofuran-1(3H),5'(4'H)-Isoxazol]-3-One

3'-Phenyl-spiro[isobenzofuran-1(3H), 5'(4'H)-isoxazol]-3-one was prepared according to the procedure of Example 2 in 30% isolated yield, m.p. 103°–106° C.

Anal. Calc'd. for $C_{16}H_{11}NO_3$: C, 72.45; H, 4.18. Found: C, 72.39; H, 4.21.

EXAMPLE 12

Preparation of 3'-(3-Trifluoromethylphenyl)-Spiro[Isobenzofuran-1(3H),5'(4'H-Isoxazol]-3-One To a solution of 109.5 g (0.75 mole) of 3-methylenephthalide and 285 g (1.27 mole) of m-trifluoromethylbenzaldehyde chlorooxime in 3.5 liters of ether was added 128.3 g (1.27 mole) of triethylamine in 250 ml. of ether at 0° C. during 3 hours. The solution was then stirred at room temperature overnight. An infrared spectrum indicated that the reaction was complete. The solid was filtered off. The ethereal solution was washed once with 10% HCl, twice with sodium chloride saturated water, dried over $CaSO_4$ and concentrated under vacuum. Only 19.5 g of impure product was obtained. The solid material which was filtered from the original reaction solution was stirred with 4 liters of tetrahydrofuran for 4 hours and filtered through a Buchner funnel. The tetrahydrofuran solution obtained was washed once with 10% HCl solution and twice with water saturated with sodium chloride. After being dried and concentrated, the tetrahydrofuran solution gave 140.6 g of pure product, m.p. 170° C.

Anal. Calc'd. for $C_{17}H_{10}F_3NO_3$: C, 61.27; H, 3.02. Found: C, 61.25; H, 3.04.

EXAMPLE 13

Preparation of 3'-(p-Fluorophenyl)-Spiro[Isobenzofuran-1(3H),5'(4'H)-Isoxazol]-3-One 3'-(p-fluorophenyl)-spiro[isobenzofuran-1(3H),5'(4'H)-isoxazol]-3-one was prepared according to the procedure of Example 1 in 65% isolated yield, m.p. 142°–145° C.

Anal. Calc'd. for $C_{16}H_{10}FNO_3$: C, 67.84; F, 3.56. Found: C, 67.89; F, 3.59.

In accordance with one aspect of the present invention, the spiro compounds of the foregoing formula have been found to be effective as herbicides. The compounds may be used by themselves or as the active ingredient in a herbicidal composition.

As used herein, the term "herbicidal active ingredient" is understood to mean a spiro compound of the foregoing formula (I).

Control of undesirable weed growth may be obtained by applying the herbicidal active ingredient to the plant locus which is defined herein to include the growth medium surrounding the plant, the seeds, emerging seedlings, roots, stems, leaves, flowers and other plant parts.

To illustrate the herbicidal properties of the compounds of the present invention, said compounds were tested in the following manner.

The pre-emergent test was conducted as follows:

A good grade of top soil was placed in aluminum pans and compacted to a depth of 0.95 to 1.27 cm. from the top of the pan. On the top of the soil was placed a predetermined number of seeds or vegetative propagules of various plant species which are compacted to a soil level. The soil required to level fill the pans after seeding or adding vegetative propagules was weighed into a pan. A known amount of the herbicidal active ingredient applied in a solvent or as a wettable powder and the soil were thoroughly mixed, and used as a cover layer for prepared pans. After treatment, the pans were moved into a greenhouse bench where they were watered from below as needed to give adequate moisture for germination and growth.

As noted in Tables I and II, below, approximately 2 or 4 weeks after seeding and treating, the plants were observed to determine all deviations from the normal growth habit and the results recorded. A herbicidal rating code was used to signify the extent of phytotoxicity of each species. The ratings are defined as follows:

| % Control | Rating |
|---|---|
| 0-24 | 0 |
| 25-49 | 1 |
| 50-74 | 2 |
| 75-100 | 3 |

The plant species utilized in these tests are identified by letter in accordance with the following legend:

| | |
|---|---|
| A - Canada Thistle | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge | Q - Wild Buckwheat |
| H - Quackgrass | R - Hemp Sesbania |
| I - Johnsongrass | S - Panicum Spp |
| J - Downy Brome | T - Crabgrass |

Results of the pre-emergent tests are summarized in Tables I and II, below.

TABLE I

| Compound of Example No. | WAT° | kg/h | A | B | C | D | E | F | G | H | I | J | K |
|---|---|---|---|---|---|---|---|---|---|---|---|---|---|
| 1 | 2 | 11.2 | 0 | 0 | 0 | 2 | 1 | 2 | 0 | 0 | 0 | 1 | 3 |
| 2 | 4 | 11.2 | 3 | 2 | 3 | 3 | 3 | 3 | 2 | 3 | 0 | 1 | 3 |
| 3 | 4 | 11.2 | 3 | 2 | 3 | 3 | 3 | 2 | 3 | 3 | 0 | 2 | 2 |
| 4 | 4 | 11.2 | 1 | 1 | 3 | 3 | 2 | 2 | 1 | 2 | 0 | 2 | 1 |
| 5 | 2 | 11.2 | 0 | 0 | 1 | 1 | 2 | 3 | 0 | 2 | 0 | 1 | 2 |
| 6 | 4 | 11.2 | 3 | 2 | 2 | 2 | 2 | 2 | 2 | 2 | 0 | 2 | 3 |
| 7 | 4 | 11.2 | 3 | 1 | 2 | 3 | 3 | 3 | 2 | 2 | 0 | 2 | 3 |
| 8 | 4 | 11.2 | 3 | — | 1 | 1 | 3 | 3 | 0 | 0 | 0 | 0 | 3 |
| 9 | 4 | 11.2 | 3 | 1 | 2 | 3 | 3 | 1 | 2 | 3 | 1 | 3 | 3 |
| 10 | 4 | 11.2 | 0 | 0 | 1 | — | 2 | 1 | 0 | 1 | 0 | 2 | 2 |
| 11 | 4 | 11.2 | 3 | 2 | 3 | 3 | 3 | 3 | 2 | 1 | 2 | 1 | 3 |
| 12 | 4 | 11.2 | 3 | 2 | 3 | 3 | 3 | 3 | 2 | 3 | 0 | 2 | 3 |
| 13 | 4 | 11.2 | 2 | — | 2 | 2 | 2 | 2 | 0 | 3 | 2 | 1 | 3 |

°Weeks after treatment.

TABLE II

| Compound of Example No. | WAT° | kg/h | L | M | N | O | P | B | Q | D | R | E | F | C | J | S | K | T |
|---|---|---|---|---|---|---|---|---|---|---|---|---|---|---|---|---|---|---|
| 1 | 2 | 5.6 | 0 | 1 | 0 | 1 | 1 | 0 | 0 | 1 | 3 | 3 | 3 | 0 | 2 | 0 | 3 | 3 |
| 1 | 2 | 1.12 | 0 | 0 | 0 | 0 | 0 | 0 | 0 | 1 | 2 | 3 | 1 | 0 | 0 | 0 | 2 | 2 |
| 2 | 4 | 5.6 | 1 | 2 | 1 | 2 | 2 | 1 | 1 | 2 | 1 | — | 3 | 2 | 1 | 0 | 3 | 0 |
| 2 | 2 | 1.12 | 0 | 2 | 0 | 1 | 0 | 0 | 0 | 2 | 0 | — | 0 | 0 | 1 | 0 | 0 | 0 |
| 2 | 2 | 0.28 | 0 | 2 | 0 | 0 | 0 | 0 | 0 | 0 | 0 | — | 0 | 0 | 0 | 0 | 0 | 0 |
| 3 | 4 | 5.6 | 0 | 3 | 3 | 2 | 2 | 1 | 0 | 0 | 1 | 3 | 2 | 3 | 3 | 3 | 3 | 3 |
| 3 | 4 | 1.12 | 0 | 2 | 2 | 1 | 1 | 1 | 1 | 2 | 0 | 3 | 0 | 2 | 2 | 2 | 2 | 2 |
| 3 | 2 | 0.28 | 1 | 2 | 1 | 1 | 0 | 0 | 1 | 0 | 0 | 3 | 1 | 0 | 0 | 0 | 1 | 2 |
| 4 | 4 | 5.6 | 1 | 3 | 1 | 2 | 2 | 0 | 3 | 1 | 3 | 3 | 3 | 2 | 0 | 1 | 1 | 3 |
| 4 | 2 | 1.12 | 1 | 3 | 0 | 0 | 0 | 0 | 2 | 0 | 1 | 3 | 1 | 1 | 0 | 0 | 1 | 1 |
| 4 | 2 | 0.28 | 0 | 1 | 0 | 0 | 0 | 0 | 0 | 0 | 0 | 2 | 0 | 0 | 0 | 0 | 0 | 1 |
| 5 | 4 | 5.6 | 2 | 3 | 1 | 1 | 2 | 0 | 3 | 1 | 2 | 3 | 3 | 1 | 1 | 0 | 3 | 1 |
| 5 | 2 | 1.12 | 0 | 1 | 0 | 1 | 0 | 0 | 2 | 0 | 0 | 3 | 3 | 0 | 0 | 0 | 0 | 3 |
| 6 | 4 | 5.6 | 1 | 2 | 0 | 1 | 0 | 1 | 2 | 0 | 1 | 2 | 3 | 1 | 0 | 1 | 2 | 3 |
| 6 | 4 | 1.12 | 0 | 2 | 0 | 2 | 1 | 0 | 1 | 1 | 2 | 2 | 3 | 0 | 3 | 0 | 2 | 3 |
| 6 | 2 | 0.28 | 0 | 1 | 0 | 1 | 0 | 0 | 1 | 1 | 0 | 1 | 0 | 0 | 0 | 1 | 1 | 1 |
| 7 | 4 | 5.6 | 3 | 3 | 2 | 3 | 2 | 2 | 2 | 2 | 2 | 2 | 3 | 2 | 2 | 2 | 3 | 3 |
| 7 | 4 | 1.12 | 0 | 2 | 0 | 0 | 0 | 0 | 0 | 2 | 0 | 0 | 0 | 1 | 3 | 0 | 0 | 0 |
| 7 | 2 | 0.28 | 0 | 1 | 0 | 0 | 0 | 0 | 0 | 1 | 0 | 2 | 0 | 1 | 0 | 0 | 0 | 2 |
| 7 | 2 | 0.056 | 0 | 1 | 0 | 0 | 0 | 0 | 0 | 0 | 0 | 1 | 1 | 0 | 0 | 0 | 0 | 1 |
| 8 | 2 | 5.6 | 0 | 1 | 0 | 0 | 0 | 3 | 2 | 3 | 2 | 3 | 0 | 0 | 0 | 0 | 3 | 2 |
| 8 | 2 | 1.12 | 0 | 1 | 0 | 0 | 0 | — | 1 | 3 | 0 | 1 | 1 | 1 | 0 | 0 | 3 | 2 |
| 8 | 2 | 0.28 | 3 | 1 | 0 | 0 | 0 | 3 | 0 | 0 | 1 | 1 | 0 | 0 | 0 | 0 | 2 | 2 |
| 9 | 4 | 5.6 | 3 | 3 | 1 | 3 | 2 | 1 | 2 | 2 | 3 | 3 | 2 | 3 | 2 | 3 | 3 | 3 |
| 9 | 4 | 1.12 | 1 | 3 | 0 | 1 | 0 | 0 | 3 | 3 | 2 | 3 | 3 | 1 | 0 | 0 | 0 | 1 |
| 9 | 4 | 0.28 | 0 | 2 | 0 | 2 | 0 | 0 | 0 | 3 | 1 | 2 | 3 | 2 | 2 | 2 | 2 | 3 |
| 10 | 2 | 5.6 | 1 | 3 | 1 | 2 | 1 | — | 0 | 0 | 1 | 3 | 3 | 2 | 1 | 1 | 2 | 3 |
| 10 | 2 | 1.12 | 1 | 2 | 0 | 2 | 0 | — | 0 | 0 | 1 | 3 | 1 | 0 | 1 | 1 | 3 | 1 |
| 10 | 2 | 0.28 | 0 | 2 | 0 | 2 | 0 | — | 0 | — | 0 | 2 | 1 | 0 | 1 | 0 | 1 | 2 |
| 11 | 4 | 5.6 | 2 | 3 | 0 | 2 | 1 | 0 | 0 | 3 | 3 | 3 | 2 | 2 | 0 | 1 | 3 | 1 |
| 11 | 4 | 1.12 | 0 | 3 | 0 | 1 | 0 | 0 | 0 | 2 | 3 | 3 | 3 | 2 | 0 | 0 | 1 | 0 |
| 11 | 2 | 0.28 | 0 | 0 | 0 | 1 | 0 | 0 | 1 | 1 | 3 | 1 | 1 | 1 | 0 | 0 | 0 | 1 |
| 12 | 4 | 5.6 | 3 | 3 | 1 | 3 | 2 | 1 | 3 | 3 | 3 | 3 | 3 | 2 | 1 | 2 | 3 | 3 |
| 12 | 4 | 1.12 | 2 | 3 | 0 | 3 | 1 | 1 | 3 | 2 | 3 | 3 | 2 | 2 | 0 | 0 | 2 | 3 |
| 12 | 2 | 0.28 | 3 | 1 | 0 | 1 | 1 | 1 | 1 | 2 | 3 | 3 | 1 | 2 | 0 | 0 | 1 | 3 |
| 13 | 4 | 5.6 | 2 | 3 | 1 | 2 | 3 | — | 3 | 1 | 3 | 3 | 3 | 1 | 1 | 0 | 3 | 3 |
| 13 | 4 | 1.12 | 1 | 2 | 1 | 1 | 2 | — | 0 | — | 1 | 0 | 0 | 1 | 0 | 1 | 1 | 1 |

TABLE II-continued

| Compound of Example No. | WAT* | kg/h | Pre-Emergent Plant Species | | | | | | | | | | | | | | |
|---|---|---|---|---|---|---|---|---|---|---|---|---|---|---|---|---|---|
| | | | L | M | N | O | P | B | Q | D | R | E | F | C | J | S | K | T |
| 13 | 2 | 0.28 | 1 | 1 | 0 | 0 | 0 | — | 0 | 0 | 0 | 1 | 1 | 0 | 0 | 0 | 0 | 0 |

*Weeks after treatment.

The post-emergent tests were conducted as follows:

The herbicidal active ingredients are applied in spray form to two or three-week old specimens of various plant species. The spray, a solution or wettable powder suspension containing the appropriate rate of herbicidal active ingredient to give the desired test rate and a surfactant, is applied to the plants. The treated plants are placed in a greenhouse and approximately two or four weeks later the effects are observed and recorded. The results are shown in Tables III and IV in which the post-emergent herbicidal rating code is as follows:

| % Control | Rating |
|---|---|
| 0–24 | 0 |
| 25–49 | 1 |
| 50–74 | 2 |
| 75–99 | 3 |
| 100 | 4 |

The plant species utilized in these tests are identified by letter in accordance with the previous legend.

TABLE III

| Compound of Example No. | WAT* | kg/h | Post-Emergent Plant Species | | | | | | | | | | |
|---|---|---|---|---|---|---|---|---|---|---|---|---|---|
| | | | A | B | C | D | E | F | G | H | I | J | K |
| 1 | 2 | 11.2 | 0 | 1 | 0 | 1 | 1 | 0 | 0 | 0 | 0 | 0 | 0 |
| 2 | 4 | 11.2 | 1 | 2 | 1 | 1 | — | 0 | 0 | 0 | 0 | 0 | 0 |
| 3 | 4 | 11.2 | 2 | 1 | 1 | 1 | 1 | 2 | 1 | 0 | 1 | 1 | 2 |
| 4 | 4 | 11.2 | 1 | 1 | 1 | 1 | 1 | 0 | 0 | 0 | 0 | 0 | 0 |
| 5 | 2 | 11.2 | 1 | 0 | 1 | 1 | 1 | 1 | 0 | 0 | 0 | 0 | 0 |
| 6 | 4 | 11.2 | 1 | 2 | 1 | 2 | 1 | 1 | 0 | 0 | 0 | 0 | 0 |
| 7 | 4 | 11.2 | 1 | 2 | 2 | 2 | 1 | 3 | 1 | 0 | 0 | 0 | 2 |
| 8 | 4 | 11.2 | 1 | 2 | 1 | 2 | 2 | 2 | 0 | 0 | 0 | 0 | 0 |
| 9 | 4 | 11.2 | 4 | 2 | 2 | 1 | 2 | 4 | 1 | 0 | 2 | 1 | 1 |
| 10 | 4 | 11.2 | 1 | 1 | 1 | 1 | 1 | 0 | 1 | 0 | 0 | 0 | 0 |
| 11 | 4 | 11.2 | 2 | 2 | 2 | 2 | 2 | 3 | 1 | 1 | 1 | 1 | 1 |
| 12 | 4 | 11.2 | 2 | 2 | 2 | 3 | 2 | 4 | 2 | 1 | 0 | 2 | |
| 13 | 4 | 11.2 | 2 | 2 | 2 | 2 | 2 | 1 | 0 | 0 | 2 | 0 | 1 |

*Weeks after treatment.

TABLE IV

| Compound of Example No. | WAT* | kg/h | Post-Emergent Plant Species | | | | | | | | | | | | | | |
|---|---|---|---|---|---|---|---|---|---|---|---|---|---|---|---|---|---|
| | | | L | M | N | O | P | B | Q | D | R | E | F | C | J | S | K | T |
| 7 | 4 | 5.6 | 2 | — | 1 | 0 | 0 | 2 | 2 | 2 | 2 | 1 | 4 | 2 | 1 | 0 | 1 | 0 |
| 7 | 2 | 1.12 | 2 | 1 | 0 | 0 | 0 | 2 | 2 | 2 | 2 | 1 | 3 | 2 | 0 | 1 | 1 | 1 |
| 7 | 2 | 0.28 | 1 | — | 0 | 0 | 0 | 1 | 1 | 1 | 1 | 1 | 2 | 1 | 0 | 0 | 1 | 0 |
| 9 | 4 | 5.6 | 2 | 2 | 1 | 1 | 2 | 2 | 4 | 2 | 4 | 3 | 4 | 2 | 1 | 1 | 2 | 1 |
| 9 | 4 | 1.12 | 2 | 1 | 0 | 1 | 0 | 2 | 2 | 2 | 2 | 2 | 4 | 2 | 0 | 0 | 1 | 0 |
| 9 | 2 | 0.056 | 0 | 1 | 0 | 1 | 0 | 0 | 0 | 0 | 3 | 2 | 0 | 1 | 0 | 0 | 1 | |
| 11 | 4 | 5.6 | 2 | 2 | 1 | 0 | 2 | 2 | 2 | 2 | — | 4 | 4 | 2 | 1 | 0 | 1 | 2 |
| 11 | 4 | 1.12 | 2 | 1 | 0 | 0 | 0 | 2 | — | 2 | 2 | 4 | 2 | 2 | 0 | 0 | 1 | 0 |
| 12 | 4 | 5.6 | 2 | 2 | 0 | 1 | 1 | 2 | 3 | 2 | — | 2 | — | 2 | 0 | 1 | 2 | 0 |
| 12 | 4 | 1.12 | 2 | 1 | 0 | 0 | 1 | — | 2 | 2 | — | 2 | 2 | 2 | 0 | 1 | 2 | 1 |
| 12 | 2 | 0.056 | 0 | 2 | 0 | 0 | 0 | 0 | 2 | 0 | 1 | 1 | 1 | 1 | 0 | 0 | 1 | 2 |
| 12 | 2 | 0.01 | 0 | 0 | 0 | 0 | 0 | — | 0 | 0 | 0 | 1 | 0 | 0 | 1 | 1 | 0 | 2 |

*Weeks after treatment.

The above tables illustrate one aspect of the present invention, that is, the use of the compounds of the invention to kill or injure undesirable plants, e.g., weeds. Another aspect of the invention, however, is the use of the spiro compounds of formula (I) for the regulation of desirable plant growth, especially leguminous plants such as soybeans. More particularly, it has been found that compounds of the foregoing formula (I) have been found to be effective in regulating the growth of leguminous plants.

As used herein, the regulation of "plant growth or development" is understood to mean the modification of the normal sequential development of a treated desirable plant to agricultural maturity. Such modifications are most readily observed as changes in size, shape, color or texture of the treated plant or any of its parts. Similarly, changes in the quantity of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growing of more plants per unit area. A darkening of the foliar color may be illustrative of higher chlorophyll activity indicative of improved rate of photosynthesis.

Although the regulation of plant growth in accordance with the present invention may include partial inhibition of plant growth when used as a plant growth regulant, it does not include the total inhibition or killing of such plants. The present invention contemplates the use of an amount of the spiro compounds of formula (I) as the active ingredient in a plant growth regulating composition which will modify the normal sequential development of the treated plant to agricultural maturity. Such plant growth regulating amounts may vary, not only with the material selected, but also with the modifying effect desired, the species of plant and its stage of development, the plant growth medium and whether a permanent or a transitory effect is sought. It is, however, well within the skill of the art to determine the amount of active ingredient required.

Modification of the plants may be accomplished by applying the active ingredient to the plant locus which has been defined herein to include the growth medium surrounding the plant, the seeds, emerging seedlings, roots, stems, leaves, flowers, or other plant parts. Such application may be made directly to the plant part, or indirectly by application to the plant growth medium.

Utilizing the spiro compounds of the formula (I) as the active ingredient in a plant growth regulating composition, said compounds were found to possess plant growth regulating activity when tested in accordance with the following procedure.

A number of soybean plants, variety Williams, were grown from seeds in plastic pots in the greenhouse for a period of one week at which time the plants are thinned to one plant per pot. When the second trifoliate leaf (three weeks) was fully expanded, the plants were treated with a solution of the active ingredient in acetone and water. Aqueous Tween 20 was used as a surfactant.

When the fifth trifoliate leaf (four to five weeks) was fully expanded, the treated plants were compared with the non-treated control plants and the observations recorded. Those observations are summarized in Table V below.

TABLE V

| Compound of Example No. | Rate (kg/h) | Observations |
|---|---|---|
| 1 | 2.8 | Stature reduction, leaf alteration of old and new growth, leaf inhibition, axillary bud inhibition, inhibition of dry weight. |
| 1 | 0.56 | Stature reduction, leaf alteration of old and new growth, leaf inhibition, axillary bud inhibition, inhibition of dry weight. |
| 1 | 0.112 | Stature reduction, leaf alteration of old and new growth, leaf inhibition, axillary bud inhibition, inhibition of dry weight. |
| 2 | 2.8 | Stature reduction, dark foliar color, leaf inhibition, leaf distortion of old and new growth, inhibition of dry weight. |
| 2 | 0.56 | Stature reduction, dark foliar color, leaf inhibition, leaf distortion of old and new growth, inhibition of dry weight. |
| 2 | 0.112 | Stature reduction, altered canopy, leaf inhibition, leaf alteration of old and new growth, inhibition of dry weight. |
| 3 | 2.8 | Stature reduction, altered canopy, leaf inhibition, leaf alteration of old and new growth, inhibition of dry weight. |
| 3 | 0.56 | Leaf alteration of old and new growth, inhibition of dry weight. |
| 3 | 0.112 | Inhibition of dry weight. |
| 4 | 2.8 | Stature reduction, inhibition of apical development, leaf inhibition, leaf alteration of new growth, epinasty, inhibition of dry weight. |
| 4 | 0.56 | Stature reduction, inhibition of apical development, leaf inhibition, leaf alteration of new growth, epinasty, inhibition of dry weight. |
| 4 | 0.112 | Stature reduction, inhibition of apical development, leaf inhibition, leaf alteration of new growth, epinasty, inhibition of dry weight. |
| 5 | 2.8 | Stature reduction, leaf inhibition, leaf alteration of old and new growth, epinasty, inhibition of dry weight. |
| 5 | 0.56 | Stature reduction, thick leaf texture, leaf alteration of old and new growth, epinasty, inhibition of dry weight. |
| 5 | 0.112 | Stature reduction, altered canopy, leaf alteration of old and new growth, epinasty, inhibition of dry weight. |
| 6 | 2.8 | Stature reduction, leaf alteration of old and new growth, dark foliar color, leaf inhibition, inhibition of dry weight. |
| 6 | 0.56 | Stature reduction, leaf alteration of old and new growth, dark foliar color, leaf inhibition, inhibition of dry weight. |
| 6 | 0.112 | Stature reduction, leaf alteration of old and new growth, leaf inhibition, inhibition of dry weight. |
| 7 | 2.8 | Stature reduction, inhibition of apical development, dark foliar color, thick leaf texture, leaf inhibition, inhibition of dry weight. |
| 7 | 0.56 | Stature reduction, inhibition of apical development, dark foliar color, leaf inhibition, leaf alteration of new growth, inhibition of dry weight. |
| 7 | 0.112 | Stature reduction, inhibition of apical development, leaf inhibition, leaf alteration of old and new growth, inhibition of dry weight. |
| 8 | 2.8 | Leaf alteration of old and new growth, leaf alteration, inhibition of dry weight. |
| 8 | 0.56 | Leaf alteration of old and new growth. |
| 8 | 0.112 | None |
| 9 | 2.8 | Stature reduction, inhibition of apical development, dark foliar color, thick leaf texture, leaf inhibition, inhibition of dry weight. |
| 9 | 0.56 | Stature reduction, inhibition of apical development, dark foliar color, thick leaf texture, leaf inhibition, inhibition of dry weight. |
| 9 | 0.112 | Stature reduction, inhibition of apical delvelopment, dark foliar color, leaf inhibition, leaf alteration of new growth, inhibition of dry weight. |
| 10 | 2.8 | Leaf alteration, leaf inhibition. |
| 10 | 0.56 | Leaf alteration. |
| 10 | 0.112 | None. |
| 11 | 2.8 | Stature reduction, inhibition of apical development, dark foliar color, thick leaf texture, leaf inhibition, inhibition of dry weight. |
| 11 | 0.56 | Stature reduction, dark foliar color, thick leaf texture, altered canopy, leaf inhibition, inhibition of dry weight. |
| 11 | 0.112 | Stature reduction, dark foliar color, thick leaf texture, altered canopy, leaf inhibition, inhibition of dry weight. |
| 12 | 2.8 | Stature reduction, leaf distortion of new growth, dark foliar color, thick leaf texture, leaf inhibition, inhibition of dry weight. |
| 12 | 0.56 | Stature reduction, leaf distortion of new growth, dark foliar color, thick leaf texture, leaf inhibition, inhibition of dry weight. |
| 12 | 0.112 | Stature reduction, leaf distortion of new growth, dark foliar color, thick leaf texture, leaf inhibition, inhibition of dry weight. |
| 13 | 2.8 | Stature reduction, leaf alteration, leaf inhibition, leaf distortion of new growth, inhibition of dry weight. |
| 13 | 0.56 | Stature reduction, leaf alteration, leaf inhibition, leaf distortion of new growth, inhibition of dry weight. |
| 13 | 0.112 | Leaf alteration of old and new growth, leaf inhibition. |

As can be seen from the above data, the spiro compounds of the invention are especially effective in reducing the stature of soybean plants as well as altering the leaf morphology.

Thus, the above data illustrate that the compounds of the invention may be used as a herbicide or a plant growth regulant. When used as a herbicide, it is desirable that rates of application about 1.12 kilograms per hectare and above be utilized. When used to regulate the growth of desirable plants, rates below 5.6 kilograms per hectare, especially 0.056 to 2.8, are preferred.

In selecting the appropriate time and rate of application of the active ingredient, it will be recognized that precise rates will also be dependent upon the desired response, mode of application, plant variety, soil conditions and various other factors known to those skilled in the art. In addition, it will be recognized that single or multiple applications may be used to exert the desired response.

In the practice of the invention, the active ingredient, whether used as a herbicide or a plant growth regulant, can be used alone or in combination with other pesticides or a material referred to in the art as an adjuvant in either liquid or solid form. To prepare such compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid or organic origin, water, a wetting agent, dispersing agent or emulsifying agent or any suitable combination of these.

Illustrative finely-divided solid carriers and extenders which are useful in the compositions of this invention include the talcs, clays, pumice, silica, diatomaceous earth, quartz, Fullers, earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The compositions can also be applied from airplanes as a dust or spray.

Compositions of this invention, whether used as a herbicide or a plant growth regulant, generally contain from about 5 to 95 parts active ingredient, about 1 to 50 parts surface-active agent and about 4 to 94 parts solvents, all parts being by weight based on the total weight of the composition.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method for preventing the growth of undesirable plants which comprises applying to the plant locus a herbicidally effective amount of a compound having the formula

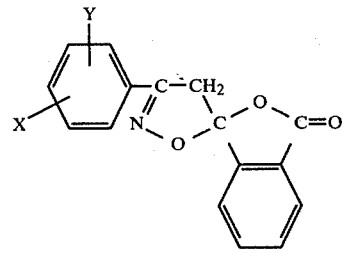

wherein X and Y are independently selected from the group consisting of hydrogen, halogen, lower alkyl, lower alkoxy, halo-lower-alkyl, phenoxy, phenyl and cyano.

2. A method according to claim 1 wherein X is hydrogen and Y is halogen, lower alkyl, lower alkoxy, halo-lower-alkyl, phenoxy, phenyl and cyano.

3. A method according to claim 1 wherein said halo-lower-alkyl is trifluoromethyl.

4. A method according to claim 1 wherein Y is halogen.

5. A method according to claim 4 wherein Y is chloro.

6. A method according to claim 4 wherein Y is fluoro.

7. A method according to claim 1 wherein Y is phenoxy.

8. A method according to claim 5 wherein X is hydrogen and Y is chloro in the para position.

9. A method according to claim 6 wherein X is hydrogen and Y is fluoro in the para position.

10. A method according to claim 7 wherein X is hydrogen and Y is phenoxy in the meta position.

11. A method according to claim 3 wherein X is hydrogen and Y is trifluoromethyl in the meta position.

* * * * *